(12) United States Patent
Schilling et al.

(10) Patent No.: US 10,292,924 B2
(45) Date of Patent: *May 21, 2019

(54) MIXTURE COMPOSITION COMPRISING RHAMNOLIPIDS

(71) Applicant: Evonik Industries AG, Essen (DE)

(72) Inventors: Martin Schilling, Bonn (DE);
Christian Hartung, Essen (DE);
Fabien Cabirol, Essen (DE); Steffen Schaffer, Herten (DE); Petra Allef, Essen (DE)

(73) Assignee: Evonik Industries AG, Essen (DE)

( * ) Notice: Subject to any disclaimer, the term of this patent is extended or adjusted under 35 U.S.C. 154(b) by 155 days.

This patent is subject to a terminal disclaimer.

(21) Appl. No.: 14/243,382

(22) Filed: Apr. 2, 2014

(65) Prior Publication Data

US 2014/0296168 A1  Oct. 2, 2014

(30) Foreign Application Priority Data

Apr. 2, 2013 (DE) .................. 10 2013 205 756

(51) Int. Cl.
*A61K 8/60* (2006.01)
*A61Q 19/00* (2006.01)
*A61Q 19/10* (2006.01)

(52) U.S. Cl.
CPC .............. *A61K 8/602* (2013.01); *A61Q 19/00* (2013.01); *A61Q 19/10* (2013.01); *A61K 2800/596* (2013.01); *A61K 2800/5922* (2013.01); *A61K 2800/86* (2013.01)

(58) Field of Classification Search
CPC ............ A61K 8/602; A61K 2800/5922; A61K 2800/596; A61K 2800/86; A61Q 19/10; A61Q 19/00
USPC ......................................................... 514/25
See application file for complete search history.

(56) References Cited

U.S. PATENT DOCUMENTS

| | | | |
|---|---|---|---|
| 3,234,258 A | 2/1966 | Morris | |
| 4,814,272 A | 3/1989 | Wagner et al. | |
| 5,075,041 A | 12/1991 | Lutz | |
| 2008/0213194 A1* | 9/2008 | DeSanto | A01N 43/16 424/49 |
| 2012/0220464 A1 | 8/2012 | Giessler-Blank et al. | |
| 2013/0035403 A1 | 2/2013 | Schaffer et al. | |
| 2013/0130319 A1* | 5/2013 | Schaffer | A01N 43/16 435/74 |
| 2014/0148588 A1 | 5/2014 | Schilling et al. | |

FOREIGN PATENT DOCUMENTS

| | | |
|---|---|---|
| CA | 2053900 | 10/1990 |
| DE | 102008001788 A1 | 11/2009 |
| EP | 0153634 | 9/1985 |
| EP | 0153634 A2 | 9/1985 |
| EP | 0499434 B1 | 8/1992 |
| EP | 1445302 A1 | 8/2004 |
| EP | 2410039 A1 | 1/2012 |
| EP | 2735605 A1 | 5/2014 |
| JP | 58217598 | 12/1983 |
| WO | WO9013533 | 11/1990 |
| WO | WO9314767 | 8/1993 |
| WO | WO0110447 A1 | 2/2001 |
| WO | WO2007115872 | 10/2007 |
| WO | WO2012010406 A1 | 1/2012 |
| WO | 2012013554 A1 | 2/2012 |
| WO | WO-2013041670 A1 * | 3/2013 .............. C12P 19/44 |

OTHER PUBLICATIONS

Rikalovic et al. (J Surfact Deterg (2013) 16:673-682).*
Sharma et al. (J. Nat. Prod. 2007, 70, 941-947).*
Rahim et al. (Molecular Microbiology (2001) 40(3), 708-718).*
Schrader, K. et al., "Grundlagen und Rezepturen der Kosnrietika" ["Principles and Formulations of Cosmetics"], 1989, 2nd edition, p. 329 to 341, Hüthig Buch Verlag Heidelberg.
European Search Report dated Aug. 5, 2014 received in a corresponding foreign application.
Ortiz, A., et al., "Effects of dirharnnolipid on the structural properties of phosphatidylcholine membranes", International Journal of Pharmaceutics 325, Nov. 2006, pp. 99-107.
Rooney, A. P., et al., "Isolation and characterization of rhamnolipid-producing bacterial strains from a biodiesel facility", FEMS Microbiol Lett, 295, Jun. 2009, pp. 82-87
Chen, M. L., et al., "Solution Self-Assembly and Adsorption at the Air-Water Interface of the Monorhanmnose and Dirhamnose Rhamnolipids and Their Mixtures", Langmuir, Dec. 2010, 26(23), pp. 18281-18292.
Ochsner, U. A., et al., "Production of Pseudomonas aeruginosa Rhamnolipid Biosurfactants in Heterologous Hosts", Appled and Environmental Microbiology, Sep. 1995, pp. 3503-3506, vol. 61, No. 9.
Heyd, M., et al., Development and trends of biosurfactant analysis and purification using rhamnolipids as an example, Anal Bioanal Chem. Jul. 2008;391(5):1579-90.
Iwasaki, K., et al., "Transformation of Pseudomonas putida by Electroporation", Biosci. Biotech. Biochem., 1994, 58(5):851-854.
International Organization for Standardization, International Standard ISO 4319, "Surface active agents—Detergents for washing fabrics—Guide for comparative testing of performance", 1st edition, Jul. 15, 1977, printed in Switzerland, 20 pages.
Japanese Office Action dated Mar. 28, 2018 issued in corresponding Japanese Patent Application No. 2014-075144.

* cited by examiner

*Primary Examiner* — Shaojia A Jiang
*Assistant Examiner* — Michael C. Henry
(74) *Attorney, Agent, or Firm* — Scully Scott Murphy and Presser

(57) ABSTRACT

The invention relates to a mixture composition comprising rhamnolipids, to a process for its preparation, to its use for producing formulations and to formulations comprising this mixture composition.

7 Claims, 1 Drawing Sheet

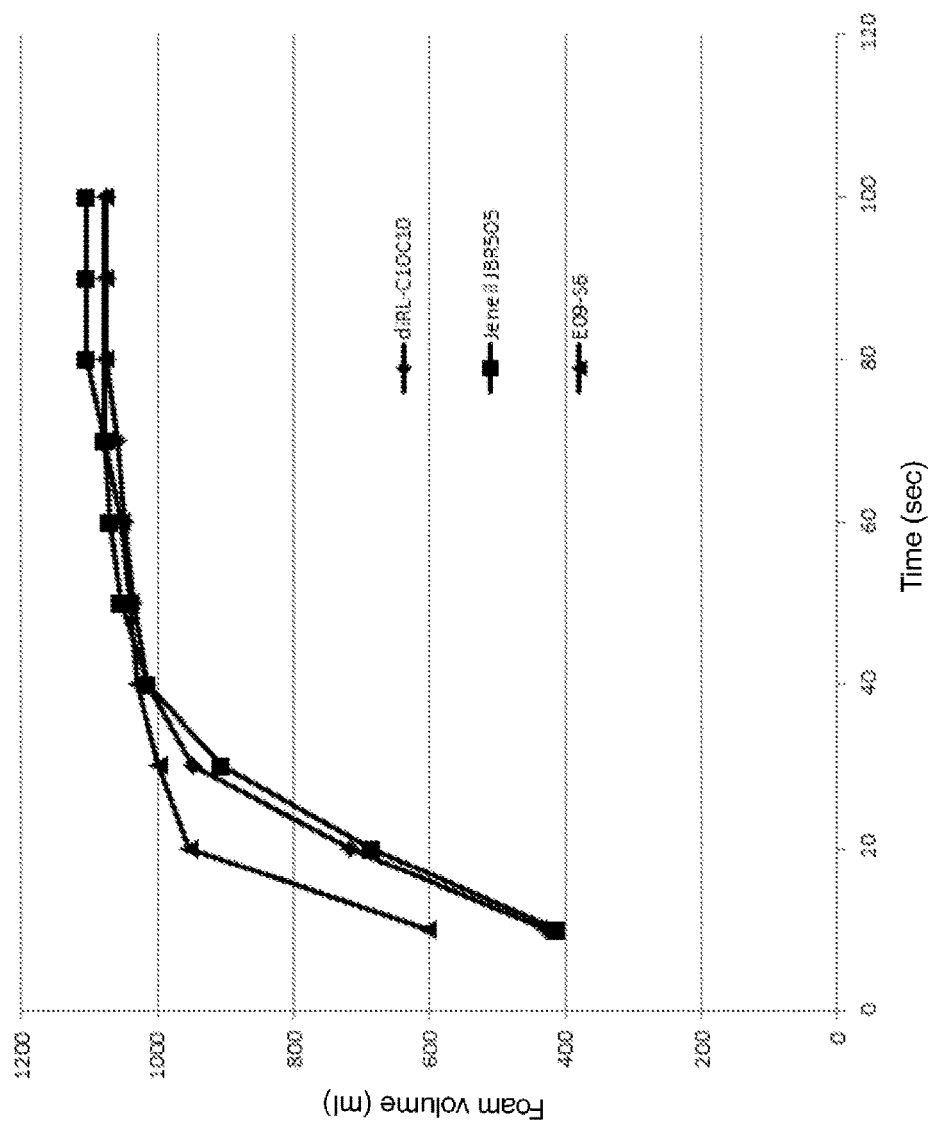

MIXTURE COMPOSITION COMPRISING RHAMNOLIPIDS

FIELD OF THE INVENTION

The present invention relates to a mixture composition comprising rhamnolipids, to a process for its preparation, to its use for producing formulations and to formulations comprising this mixture composition.

PRIOR ART

Rhamnolipids are glycolipids which are produced in free nature from certain bacteria, for example *Pseudomonas aeruginosa*. The microorganisms usually produce mixtures of rhamnolipids comprising mono- and di-rhamnolipids which have one or two rhamnose units per molecule and can contain lipid chains of different length.

EP153634 describes a mixture composition with an almost balanced weight ratio of mono- to di-rhamnolipids.

Likewise, EP0499434 describes, in Example 3, rhamnolipid compositions with a balanced weight ratio of the two components.

EP2410039 describes cleaning compositions comprising mono- and di-rhamnolipids with a weight ratio of 95:5 to 45:55.

The characterization of the surface activities of pure di-rhamnolipids, pure mono-rhamnolipids and mixtures are described, for example, in Chen et al., *Solution self-assembly and adsorption at the air-water interface of the monorhamnose and dirhamnose rhamnolipids and their mixtures*, Langmuir. 2010 Dec. 7; 26(23):18281-92.

A disadvantage of the hitherto known rhamnolipids preparable by simple fermentative processes is their relatively small fraction of di-rhamnolipids.

In addition to this, these rhamnolipid compositions often comprise rhamnolipids with only one acyl chain as undesired by-products.

Pure di-rhamnolipid compositions purified by fractionation are characterized upon use as a cosmetic by a rough, dry skin feel.

Rhamnolipid compositions which have good foam properties and have a light skin feel when used in skin care compositions or skin cleansing compositions are thus needed.

SUMMARY OF THE INVENTION

Surprisingly, it has been found that the mixture composition described below is able to exhibit good foam properties and have a light skin feel when used in compositions for skin care and skin cleansing.

The present invention therefore provides mixture compositions comprising certain rhamnolipids in defined weight ratios.

The invention further provides a process for preparing the mixture compositions according to the invention using genetically modified cells.

The present invention further provides formulations comprising the mixture compositions according to the invention.

A first advantage of the mixture compositions according to the invention is their excellent foam stability under aqueous conditions.

A second advantage of the mixture compositions according to the invention is their outstanding foam volume under aqueous conditions.

A third advantage of the mixture compositions according to the invention is their exceptional foaming behavior.

A fourth advantage of the mixture compositions according to the invention is their simple formulatability in any desired aqueous surface-active systems.

A fifth advantage of the mixture compositions according to the invention is their good thickenability with conventional thickeners in formulations.

A sixth advantage is their good ability to wash off skin and hair.

A seventh advantage of the mixture compositions according to the invention is their mildness and good physiological compatibility, in particular characterized by a high value in the red blood cell (RBC) test.

An eighth advantage is their good skin feel during and after washing.

A ninth advantage of the mixture compositions according to the invention is that they leave behind a soft skin feel after washing.

A tenth advantage of the mixture compositions according to the invention is that they leave behind a smooth skin feel after washing.

An eleventh advantage of the mixture compositions according to the invention is that they have a refatting effect on the skin.

A twelfth advantage of the mixture compositions according to the invention is that they can be synthesized essentially free from oil.

BRIEF DESCRIPTION OF THE DRAWINGS

FIG. 1, the sole FIGURE of the present application, illustrates the foaming behavior with SITA measurement for exemplary mixture compositions of the present invention and not of the present invention.

DETAILED DESCRIPTION

In connection with the present invention, the term "rhamnolipid" is understood as meaning in particular compounds of general formula (I) or salts thereof,

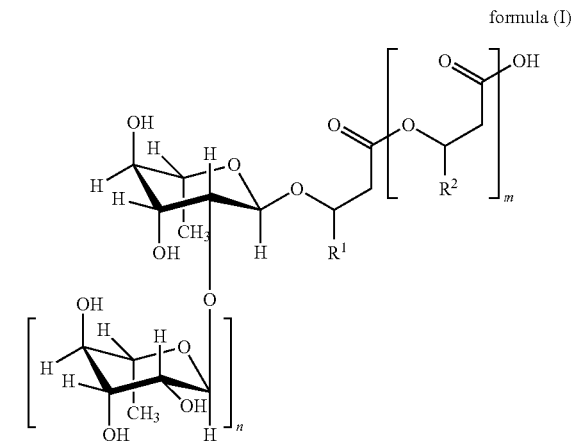

formula (I)

where
m=2, 1 or 0,
n=1 or 0,
$R^1$ and $R^2$=independently of one another, identical or different organic radical having 2 to 24, preferably 5 to 13, carbon atoms, in particular optionally branched, optionally substituted, in particular hydroxy-substituted, optionally unsaturated, in particular optionally mono-, di- or triunsaturated, alkyl radical, preferably one selected from the group consisting of pentenyl, heptenyl, nonenyl, undecenyl and tridecenyl and $(CH_2)_o$—$CH_3$ where o=1 to 23, preferably 4 to 12.

In connection with the present invention, the term "di-rhamnolipid" is understood as meaning compounds of general formula (I) or salts thereof in which n=1.

In connection with the present invention, the term "mono-rhamnolipid" is understood as meaning compounds of general formula (I) or salts thereof in which n=0.

Distinct rhamnolipids are abbreviated according to the following nomenclature: "diRL-CXCY" is understood as meaning di-rhamnolipids of general formula (I) in which one of the radicals $R^1$ and $R^2$=$(CH_2)_o$—$CH_3$ where o=X-4 and the remaining radical $R^1$ or $R^2$=$(CH_2)_o$—$CH_3$ where o=Y-4.

"monoRL-CXCY" is understood as meaning mono-rhamnolipids of general formula (I) in which one of the radicals $R^1$ and $R^2$=$(CH_2)_o$—$CH_3$ where o=X-4 and the remaining radical $R^1$ or $R^2$=$(CH_2)_o$—$CH_3$ where o=Y-4.

The nomenclature used thus does not differentiate between "CXCY" and "CYCX".

For rhamnolipids where m=0, monoRL-CX or diRL-CX is accordingly used.

If one of the aforementioned indices X and/or Y is provided with ":Z", then this means that the respective radical $R^1$ and/or $R^2$=an unbranched, unsubstituted hydrocarbon radical with X-3 or Y-3 carbon atoms having Z double bonds.

In connection with the present invention, the "pH" is defined as the value which is measured for a corresponding substance at 25° C. after stirring for five minutes using a pH electrode calibrated in accordance with ISO 4319 (1977).

In connection with the present invention, the term "aqueous medium" is understood as meaning a composition which comprises at least 5% by weight of water, based on the total composition under consideration.

Unless stated otherwise, all the stated percentages (%) are percentages by mass.

The present invention provides a mixture composition comprising rhamnolipids, characterized in that the mixture composition comprises 51% by weight to 95% by weight, preferably 70% by weight to 90% by weight, particularly preferably 75% by weight to 85% by weight, of diRL-C10C10 and
0.5% by weight to 9% by weight, preferably 0.5% by weight to 3% by weight, particularly preferably 0.5% by weight to 2% by weight, of monoRL-C10C10
where the percentages by weight refer to the sum of all of the rhamnolipids present, with the proviso that the weight ratio of di-rhamnolipids to mono-rhamnolipids is greater than 91:9, preferably greater than 97:3, particularly preferably greater than 98:2.

A preferred mixture composition according to the invention is characterized in that the mixture composition comprises 0.5% by weight to 15% by weight, preferably 3% by weight to 12% by weight, particularly preferably 5% by weight to 10% by weight, of diRL-C10C12:1, where the percentages by weight refer to the sum of all of the rhamnolipids present.

A further preferred mixture composition according to the invention is characterized in that the mixture composition comprises 0.5 to 25% by weight, preferably 5% by weight to 15% by weight, particularly preferably 7% by weight to 12% by weight, of diRL-C10C12, where the percentages by weight refer to the sum of all of the rhamnolipids present.

It is also preferred if the mixture composition according to the invention comprises 0.1% by weight to 5% by weight, preferably 0.5% by weight to 3% by weight, particularly preferably 0.5% by weight to 2% by weight, of monoRL-C10C12 and/or, preferably and 0.1% by weight to 5% by weight, preferably 0.5% by weight to 3% by weight, particularly preferably 0.5% by weight to 2% by weight, of monoRL-C10C12:1, where the percentages by weight refer to the sum of all of the rhamnolipids present.

It may be advantageous and is therefore preferred if the mixture composition according to the invention comprises 0.1% by weight to 25% by weight, preferably 2% by weight to 10% by weight, particularly preferably 4% by weight to 8% by weight, of diRL-C8C10, where the percentages by weight refer to the sum of all of the rhamnolipids present.

A particularly preferred mixture composition according to the invention is characterized in that the mixture composition comprises 0.5% by weight to 15% by weight, preferably 3% by weight to 12% by weight, particularly preferably 5% by weight to 10% by weight, of diRL-C10C12:1,
0.5 to 25% by weight, preferably 5% by weight to 15% by weight, particularly preferably 7% by weight to 12% by weight, of diRL-C10C12, 0.1% by weight to 5% by weight, preferably 0.5% by weight to 3% by weight, particularly preferably 0.5% by weight to 2% by weight, of monoRL-C10C12 and
0.1% by weight to 5% by weight, preferably 0.5% by weight to 3% by weight, particularly preferably 0.5% by weight to 2% by weight, of monoRL-C10C12:1,
where the percentages by weight refer to the sum of all of the rhamnolipids present.

Over and above this, it is preferred if the mixture composition according to the invention comprises rhamnolipids of the formula monoRL-CX or diRL-CX in only small amounts. In particular, the mixture composition according to the invention comprises preferably 0% by weight to 5% by weight, preferably 0% by weight to 3% by weight, particularly preferably 0% by weight to 1% by weight, of diRLC10, where the percentages by weight refer to the sum of all of the rhamnolipids present, and the term "0% by weight" is to be understood as meaning no detectable amount.

The mixture composition according to the invention preferably comprises at least 60% by weight, preferably at least 80% by weight, particularly preferably at least 90% by weight, in particular at least 95% by weight, of rhamnolipids, where the percentages by weight refer to the dry substance of the overall mixture composition.

It is preferred according to the invention that the mixture compositions according to the invention are essentially free from a fatty oil (acyl glycerols liquid at 20° C.) and therefore comprise in particular less than 0.5% by weight, in particular less than 0.1% by weight, particularly preferably no detectable amounts, of fatty oil, based on the overall mixture composition.

The mixture compositions according to the invention can be prepared by mixing the pure substances, in which case the pure substances can be purified from conventionally prepared rhamnolipid mixtures. Corresponding purification processes are, for example, selective crystallizations and chromatographic methods. Corresponding processes are described in Heyd et al., *Development and trends of biosurfactant analysis and purification using rhamnolipids as an example*, Anal Bioanal Chem. 2008 July; 391(5):1579-90.

In particular, the processes described below, which are likewise subject matter of the present invention, are suitable for preparing mixture compositions according to the invention.

The process according to the invention comprises the process steps:

Ia) providing a *Pseudomonas putida* cell which has been genetically modified in such a way that it overexpresses in each case at least one gene of the group rhlA, rhlB and rhlC, IIa) bringing the cell according to the invention into contact with a medium comprising at least one carbon source, IIIa) cultivating the cell under conditions which allow the cell to form rhamnolipid from the carbon source, and IVa) optionally isolating the rhamnolipids formed, characterized in that the gene rhlC is overexpressed more compared to rhlB, in particular at least 1.5 times more, preferably at least 2 times more, particularly preferably at least 10 times more.

The relative intensity of the overexpression described above can be determined for example with the help of RT-PCR, in which the amount of formed mRNA is determined for the respective gene.

A person skilled in the art can achieve a regulation of the intensity of the expression in a targeted manner for example through the selection of promoters or through the use of inducible promoters in combination with an amount of inductor, or else by means of gene multiplications.

A likewise preferred, alternative process according to the invention comprises the process steps:

Ib) providing a *Pseudomonas putida* cell which has been genetically modified such that it has in each case at least one exogenous gene of the group rhlA, rhlB and rhlC, of which at least one is under the control of an inducible promoter, IIb) bringing the cell according to the invention into contact with, and cultivating it with a medium comprising at least one carbon source while achieving a cell density of 1-30 g of cell dry mass per L of fermentation broth, preferably 2-20 g of cell dry mass per L of fermentation broth, particularly preferably 5-15 g of cell dry mass per L of fermentation broth, IIIb) inducing the at least one inducible promoter and cultivating the cell under conditions which allow the cell to form rhamnolipid from the carbon source, and IVb) optionally isolating the rhamnolipids formed.

In connection with the present invention, the term "inducible promoter" is understood as meaning a promoter which changes its activity by changing the medium surrounding the cell. Changes can include for example temperature changes and concentration changes of certain substances.

In connection with the present invention, the term "inducing the at least one inducible promoter" is to be understood as meaning that the activity of the inducible promoter is increased by changing the medium surrounding the cell.

Suitable inducible promoters that can be employed in the present invention are, for example, promoters which are induced by adding chemical inducers (for example, lactose, IPTG, dicyclopropyl ketone, tetracyclin, doxycyclin, propionate, cumate, benzoate, arabinose, rhamnose, nicotinic acid, etc.), which are induced by altered environmental conditions (for example, occurrence of phosphate or sulphur deficiency, altered temperatures or pH, etc.), or which are induced by certain physiological states (for example, certain cell densities or growth rates or phases).

Inducible promoters that can be used in the process are selected from the group of promoters inducible by dicyclopropyl ketone, tetracyclin, doxycyclin, propionate, cumate, benzoate, phosphate deficiency, sulphur deficiency or a reduced growth rate.

The genes rhlA, rhlB and rhlC in both processes according to the invention are preferably selected from those from *P. aeruginosa*.

The two processes according to the invention are preferably not carried out as biotransformation; this means that the rhamnolipids are not formed from fatty acids or fatty-acid-containing compounds such as, for example, fats and oils, that are introduced to the process from outside, but that the carbon sources specified in the processes are in particular to be understood as meaning those which contain predominantly at least one carbon-containing compound other than fatty acids or fatty-acid-containing compounds.

The mixture compositions according to the invention can advantageously be incorporated into cosmetic formulations.

Consequently, a further subject matter of the present invention is the use of the mixture compositions according to the invention for producing formulations, in particular cosmetic formulations, and also the formulations, in particular cosmetic formulations, which comprise the mixture composition according to the invention.

Besides the mixture compositions according to the invention, preferred formulations according to the invention comprise at least one further surfactant, it being possible to use, for example, anionic, nonionic, cationic and/or amphoteric surfactants. Preferably, from an applications-related point of view, preference is given to mixtures of anionic and nonionic surfactants. The total surfactant content of the aqueous formulation is preferably 5 to 60% by weight and particularly preferably 15 to 40% by weight, based on the total formulation.

The nonionic surfactants used are preferably alkoxylated, advantageously ethoxylated, in particular primary alcohols having preferably 8 to 18 carbon atoms and on average 1 to 12 mol of ethylene oxide (EO) per mol of alcohol, in which the alcohol radical can be linear or preferably 2-position methyl-branched or can contain linear and methyl-branched radicals in a mixture, as are customarily present in oxo alcohol radicals. In particular, however, alcohol ethoxylates with linear radicals from alcohols of native origin having 12 to 18 carbon atoms, for example, from coconut, palm, tallow fat or oleyl alcohol, and on average 2 to 8 EO per mol of alcohol are preferred. The preferred ethoxylated alcohols include, for example, C12-C14-alcohols with 3 EO, 4 EO or 7 EO, C9-C11-alcohol with 7 EO, C13-C15-alcohols with 3 EO, 5 EO, 7 EO or 8 EO, C12-C18-alcohols with 3 EO, 5 EO or 7 EO and mixtures of these, such as mixtures of C12-C14-alcohol with 3 EO and C12-C18-alcohol with 7 EO. The stated degrees of ethoxylation are statistical average values which can be an integer or a fraction for a specific product. Preferred alcohol ethoxylates have a narrowed homolog distribution.

In addition to these nonionic surfactants, it is also possible to use fatty alcohols with more than 12 EO. Examples of such fatty acids are tallow fatty alcohol with 14 EO, 25 EO, 30 EO or 40 EO.

Nonionic surfactants which contain EO and PO (propylene oxide) groups together in the molecule can also be used. In this connection, it is possible to use block copolymers with EO-PO block units or PO-EO block units, but also EO-PO-EO copolymers or PO-EO-PO copolymers.

It is of course also possible to use mixed alkoxylated nonionic surfactants in which EO and PO units are not distributed blockwise, but randomly. Such products are obtainable as a result of the simultaneous action of ethylene oxide and propylene oxide on fatty alcohols.

Furthermore, alkyl glycosides can also be used as further nonionic surfactants.

A further class of preferably used nonionic surfactants, which are used either as the sole nonionic surfactant or in combination with other nonionic surfactants, are alkoxylated, preferably ethoxylated or ethoxylated and propoxylated fatty acid alkyl esters, preferably having 1 to 4 carbon atoms in the alkyl chain, in particular fatty acid methyl esters, as are described for example in the Japanese patent application JP 58/217598 or which are preferably prepared by the process described in the international patent application WO-A-90/13533.

Nonionic surfactants of the amine oxide type, for example, N-cocoalkyl-N,N-dimethylamine oxide and N-tallowalkyl-N,N-dihydroxyethylamine oxide, and of the fatty acid alkanolamide type may also be suitable. The amount of these nonionic surfactants is preferably not more than that of the ethoxylated fatty alcohols, in particular not more than half thereof.

Further suitable surfactants are polyhydroxy fatty acid amides; the polyhydroxy fatty acid amides are substances which can usually be obtained by reductive amination of a reducing sugar with ammonia, an alkylamine or an alkanolamine and subsequent acylation with a fatty acid, a fatty acid alkyl ester or a fatty acid chloride.

The anionic surfactants used are, for example, those of the sulphonate and sulphate type. Suitable surfactants of the sulphonate type include C9-C13-alkylbenzenesulphonates, olefinsulphonates, i.e., mixtures of alkene- and hydroxyalkanesulphonates, and also disulphonates, as are obtained, for example, from C12-C18-monoolefins with a terminal or internal double bond by sulphonation with gaseous sulphur trioxide and subsequent alkaline or acidic hydrolysis of the sulphonation products. Also of suitability are alkanesulphonates which are obtained from C12-C18-alkanes, for example, by sulphochlorination or sulphoxidation with subsequent hydrolysis or neutralization. Similarly, the esters of α-sulpho fatty acids (ester sulphonates), for example, the α-sulphonated methyl esters of hydrogenated coconut, palm kernel or tallow fatty acids, are also suitable.

Further suitable anionic surfactants are sulphated fatty acid glycerol esters. Fatty acid glycerol esters are to be understood as meaning the mono-, di- and triesters, and also mixtures thereof, as are obtained in the preparation by esterification of a monoglycerol with 1 to 3 mol of fatty acid or in the transesterification of triglycerides with 0.3 to 2 mol of glycerol. Preferred sulphated fatty acid glycerol esters that can be employed are the sulphation products of saturated fatty acids having 6 to 22 carbon atoms, for example, of caproic acid, caprylic acid, capric acid, myristic acid, lauric acid, palmitic acid, stearic acid or behenic acid.

Preferred alk(en)yl sulphates are the alkali metal and in particular the sodium salts of the sulphuric acid half-esters of the C12-C18-fatty alcohols, for example, from coconut fatty alcohol, tallow fatty alcohol, lauryl, myristyl, cetyl or stearyl alcohol or the C10-C20-oxo alcohols and those half-esters of secondary alcohols of these chain lengths. Furthermore, preference is given to alk(en)yl sulphates of the specified chain length which contain a synthetic straight-chain alkyl radical prepared on a petrochemical basis, and which have an analogous degradation behavior to the suitable compounds based on fatty chemical raw materials. From the point of view of washing, the C12-C16-alkyl sulphates and C12-C18-alkyl sulphates and also C14-C18-alkyl sulphates are preferred. 2,3-Alkyl sulphates, which are prepared for example in accordance with the U.S. Pat. Nos. 3,234,258 or 5,075,041 and can be obtained as commercial products of the Shell Oil Company under the name DAN®, are also suitable anionic surfactants.

The sulphuric acid monoesters of the straight-chain or branched C7-C20-alcohols ethoxylated with 1 to 6 mol of ethylene oxide, such as 2-methyl-branched C9-C11-alcohols having on average 3.5 mol of ethylene oxide (EO) or C12-C18-fatty alcohols with 1 to 4 EO, are also suitable. On account of their high foaming behavior, they are used in cleaning compositions only in relatively small amounts, for example in amounts of from 1 to 5% by weight.

Further suitable anionic surfactants are the salts of alkylsulphosuccinic acid, which are also referred to as sulphosuccinates or as sulphosuccinic acid esters and constitute the monoesters and/or diesters of sulphosuccinic acid with alcohols, preferably fatty alcohols and in particular ethoxylated fatty alcohols. Preferred sulphosuccinates contain C8-C18-fatty alcohol radicals or mixtures of these. Particularly preferred sulphosuccinates contain a fatty alcohol radical which is derived from ethoxylated fatty alcohols. In this connection, sulphosuccinates whose fatty alcohol radicals are derived from ethoxylated fatty alcohols with a narrow homolog distribution are particularly preferred in turn. It is likewise also possible to use alk(en)ylsuccinic acid having preferably 8 to 18 carbon atoms in the alk(en)yl chain or salts thereof.

Particularly preferred anionic surfactants are soaps. Also of suitability are saturated and unsaturated fatty acid soaps, such as the salts of lauric acid, myristic acid, palmitic acid, stearic acid, (hydrogenated) erucic acid and behenic acid, and also soap mixtures derived in particular from natural fatty acids, for example coconut, palm kernel, olive oil or tallow fatty acid.

The anionic surfactants including the soaps can be in the form of their sodium, potassium or ammonium salts, as well as soluble salts of organic bases, such as mono-, di- or triethanolamine. Preferably, the anionic surfactants are in the form of their sodium or potassium salts, in particular in the form of the sodium salts.

Amphoteric surfactants which can be used according to the invention are those surface-active compounds which carry at least one quaternary ammonium group and at least one —COO⁻— or —SO₃⁻ group in the molecule. Particularly preferred amphoteric surfactants in this connection are betaine surfactants such as alkyl- or alkylamidopropylbetaines. In particular, betaines such as the N-alkyl-N,N-dimethylammonium glycinates, e.g., the cocoalkyldimethylammonium glycinate, N-acylaminopropyl-N,N-dimethylammonium glycinates, e.g. the cocoacylaminopropyldimethylammonium glycinate, the C12-C18-alkyldimethylacetobetaine, the cocoamidopropyldimethylacetobetaine, 2-alkyl-3-carboxymethyl-3-hydroxyethylimidazolines and sulphobetaines having in each case 8 to 18 carbon atoms in the alkyl or acyl group, and also the cocoacylaminoethylhydroxyethylcarboxymethyl glycinate are preferred. A particularly preferred zwitterionic surfactant is the N,N-dimethyl-N-(lauroylamidopropyl)ammoniumacetobetaine known under the INCI name Cocamidopropyl Betaine.

Further suitable amphoteric surfactants are formed by the group of amphoacetates and amphodiacetates, in particular, for example, coco- or laurylamphoacetates or -diacetates, the group of amphopropionates and amphodipropionates, and the group of amino acid-based surfactants such as acyl glutamates, in particular disodium cocoyl glutamate and sodium cocoyl glutamate, acyl glycinates, in particular cocoyl glycinates, and acyl sarcosinates, in particular ammonium lauroyl sarcosinate and sodium cocoyl sarcosinate.

Furthermore, the formulations according to the invention can comprise at least one additional component selected from the group of emollients, emulsifiers, thickeners/viscosity regulators/stabilizers, UV photoprotective filters, antioxidants, hydrotropes (or polyols), solids and fillers, film formers, pearlescent additives, deodorant and antiperspirant active ingredients, insect repellents, self-tanning agents, preservatives, conditioners, perfumes, dyes, odour absorbers, cosmetic active ingredients, care additives, superfatting agents, solvents.

Substances which can be used as exemplary representatives of the individual groups are known to the person skilled in the art and can be found for example in German application DE 102008001788.4. This patent application is hereby incorporated by reference and thus forms part of the disclosure.

Concerning further optional components and the amounts of these components used, reference is made expressly to the relevant handbooks known to the person skilled in the art, for example K. Schrader, "Grundlagen and Rezepturen der Kosmetika [Fundamentals and Formulations of Cosmetics]", 2nd edition, page 329 to 341, Hüthig Buch Verlag Heidelberg.

The amounts of the respective additives are dependent on the intended use.

Typical guide formulations for the respective applications are known prior art and are contained for example in the brochures of the manufacturers of the respective base materials and active ingredients. These existing formulations can generally be adopted unchanged. If required, however, the desired modifications can be undertaken without complication by means of simple experiments for the purposes of adaptation and optimization.

The mixture compositions according to the invention and the formulations according to the invention comprising the mixture composition according to the invention can advantageously be used for the cleaning of surfaces. In this form of the use according to the invention, the surface is preferably the surface of a living being, in particular of a person, with such surfaces particularly preferably being selected from skin and hair.

The examples listed below describe the present invention by way of example without any intention of limiting the invention, the scope of application of which arises from the entire description and the claims, to the embodiments specified in the examples.

EXAMPLES

Example 1

Preparation of diRL-C10C10 and monoRL-C10-C10

The preparation of the various pure RL forms took place by means of preparative column chromatography. For this, 750 g of a silica 60 gel (200-500 µm; 35-70 mesh; Sigma-Aldrich, Germany) were suspended in water-saturated ethyl acetate (acidified with 1% by weight of acetic acid) and poured into a column (diameter=65 mm, maximum fill level=600 mm, 1 l solvent reservoir). 2-3 cm of acid-treated sea sand (Riedel de Haen, Seelze, Germany) were coated as protective layer over the stationary phase. The eluent used was likewise water-saturated ethyl acetate which comprises 1% by weight of acetic acid. A commercially available RL mixture (JBR 505, Jeneil Biosurfactants, ~5% by weight total rhamnolipid concentration) was freeze-dried.

10 g of the freeze-dried RL mixture were dissolved in 5% by weight concentration in the eluent. The solution was placed onto the prepared column. The eluent flow rate was adjusted to 15 ml/min. The eluate was collected in 100 ml fractions and analyzed by means of thin-film chromatography and HPLC. The various RL forms can be separated in this way. Fractions of identical composition were combined and the solvent was stripped off on a rotary evaporator. Then, the residue was dissolved in water, freeze-dried and used in powder form for the application tests. In order to obtain adequate amounts, this procedure was carried out several times. The purity of the resulting fractions was determined as >99% by weight by means of $^1$H-NMR and HPLC.

Example 2

Preparation of a Mixture of diRL-C10C10 and monoRL-C10C10

The pure RL forms described in Example 1 were mixed in powder form in a ratio of diRL-C10C10 to monoRL-C10C10 of 97.5:2.5.

Example 3

Preparation of Rhamnolipids with rhlABC from *P. Aeruginosa* PAO1 in *P. Putida*, where the Expression of the Gene Coding for the Rhamnosyltransferase RhlC is Many Times More than that of the Gene rhlB Coding for the Rhamnosyltransferase RhlB In order to prepare rhamnolipids with rhlABC from *P. aeruginosa* PAO1 in a *P. putida* strain in which the expression of the gene coding for the rhamnosyltransferase RhlC took place to a much greater extent than that of the gene rhlB coding for the rhamnosyltransferase RhlB, the plasmid pBBR1MCS2-Plac-rhlABC-T-Ptac-rhlC-T (Seq ID No. 1) was constructed. For this, the following DNA fragments were synthesized:

*P. aeruginosa* PAO1 genes rhlA, rhlB and rhlC, followed by a terminator, followed by the synthetic tac promoter, followed by the *P. aeruginosa* PAO1 gene rhlC and a terminator, flanked by a HindIII restriction site (5' end) or Bsu36I restriction site (3' end) (Seq ID No. 2).

The vectors provided by the DNA synthesis provider and which contain the synthesized DNA fragment were cleaved with HindIII and Bsu36I and ligated into the vector pBBR1MCS-2 (Seq ID 3), likewise cleaved with HindIII and Bsu36I, by means of a Fast Link Ligation Kit (Epicentre Technologies; Madison, Wis., USA). The resulting target vector pBBR1MCS2-Plac-rhlABC-T-Ptac-rhlC-T (pBBR1MCS-2 with synthesized fragment Seq ID No. 2) had a size of 9336 base pairs.

The transformation of *Pseudomonas putida* KT2440 with the vector pBBR1MCS2-Plac-rhlABC-T-Ptac-rhlC-T (Seq ID No. 1) took place as described above (Iwasaki et al. Biosci. Biotech. Biochem. 1994. 58(5):851-854). The plasmid DNA from 10 clones in each case was isolated and analyzed. The resulting strain carrying the plasmid was called *P. putida* KT2440 pBBR1MCS2-Plac-rhlABC-T-Ptac-rhlC-T.

The recombinant strain *P. putida* KT2440 pBBR1MCS2-Plac-rhlABC-T-Ptac-rhlC-T was cultivated on LB-agar-canamycin (50 µg/ml) plates.

For the production of the rhamnolipids, the medium referred to below as M9 medium was used. This medium consists of 2% (w/v) glucose, 0.3% (w/v) $KH_2PO_4$, 0.679% $Na_2HPO_4$, 0.05% (w/v) NaCl, 0.2% (w/v) $NH_4Cl$, 0.049% (w/v) $MgSO_4 \times 7H_2O$ and 0.1% (v/v) of a trace element solution. This consists of 1.78% (w/v) $FeSO_4 \times 7H_2O$, 0.191% (w/v) $MnCl_2 \times 7\ H_2O$, 3.65% (w/v) HCl, 0.187% (w/v) $ZnSO_4 \times 7H_2O$, 0.084% (v/v) $Na-EDTA \times 2H_2O$, 0.03% (v/v) $H_3BO_3$, 0.025% (w/v) $Na_2MoO_4 \times 2H_2O$ and 0.47% (w/v) $CaCl_2 \times 2\ H_2O$. The pH of the medium was adjusted to 7.4 with $NH_4OH$ and the medium was consequently sterilized by means of an autoclave (121° C., 20 min). Adjustment of the pH during the cultivation was not necessary.

To investigate the rhamnolipid production in the shake flask, firstly a preculture was prepared. For this, a colony of a strain freshly streaked on LB-agar plate was used and 10 ml of LB medium was inoculated in a 100 ml Erlenmeyer flask. All of the recombinant *P. putida* strains were cultivated in the LB medium to which 50 µg/ml of canamycin was added. The *P. putida* strains were cultivated overnight at 30° C. and 200 rpm.

The precultures were used in order to inoculate 50 ml of M9 medium (+50 µg/ml canamycin) in the 250 ml Erlenmeyer flask (starting $OD_{600}$ 0.1). The cultures were cultivated at 200 rpm and 30° C. After 24 h, a sample of 1 ml of culture broth was removed from the culture flask.

Fermentation and Purification

A mineral medium (M9) was likewise used for the main culture. The fermentation following inoculation with 10% by volume of preculture and consumption of the initially introduced glucose took place with carbon limitation via a glucose feeding in a 2 liter fermenter with an operating volume of 1.2 L. The glucose feeding took place by reference to the dissolved oxygen signal. The dissolved oxygen was regulated at 20% saturation via the stirrer speed. The pH was regulated to 7 via a pH electrode and addition of $NH_4SO_4$. The fermentation was conducted over 4 days to a bio dry mass of 15 g/l. The rhamnolipid concentration was ascertained via HPLC and was 9.8 g/l. After separating off the cells by means of centrifugation at 10 000 g, the fermentation broth was adjusted to a pH of 4.0 by adding concentrated HCl. Extraction was then carried out with the same volume of ethyl acetate. The rhamnolipid-containing organic phase was separated off and further processed. The pH of the solution was adjusted to pH 7 by adding 50% strength by weight KOH (aq). This resulted in the formation of two liquid phases. The lower phase contained the rhamnolipids freed from lipophilic and hydrophilic impurities in high purity. The composition of the RL mixture was not influenced as a result of this. The lower phase was drawn off and the solvent was largely removed on a rotary evaporator. Water was then added again and the aqueous RL solution was freeze-dried. The resulting powder was analyzed by means of HPLC and characterized as to application.

Quantification of Rhamnolipids

Sample preparation for the following chromatographic analyzes took place as follows. A displacement pipette (Combitip) was used to initially introduce 1 ml of acetone in a 2 ml reaction vessel, and the reaction vessel was closed immediately to minimize evaporation. Next, 1 ml of culture broth was added. After vortexing the culture broth/acetone mixture, it was centrifuged for 3 min at 13 000 rpm, and 800 µl of the supernatant was transferred to a HPLC vessel.

For the purposes of detection and quantification of rhamnolipids, an evaporative light scattering detector (Sedex LT-ELSD model 85LT) was used. The actual measurement was carried out by means of Agilent Technologies 1200 Series (Santa Clara, Calif.) and the Zorbax SB-C8 Rapid Resolution Column (4.6×150 mm, 3.5 µm, Agilent). The injection volume was 5 µl and the run time of the method was 20 min. The mobile phase used was aqueous 0.1% TFA (trifluoroacetic acid, solution A) and methanol (solution B). The column temperature was 40° C. Serving as detectors were the ELSD (detector temperature 60° C.) and the DAD (diode array, 210 nm). The gradient used in the method was:

| t [min] | Solution B % by volume | Flow rate [ml/min] |
| --- | --- | --- |
| 0.00 | 70% | 1.00 |
| 15.00 | 100% | 1.00 |
| 15.01 | 70% | 1.00 |
| 20.00 | 70% | 1.00 |

The rhamnolipid composition from *P. putida* KT2440 pBBR1MCS2-Plac-rhlABC-T-Ptac-rhlC-T obtained with the process described above comprises:

| | |
| --- | --- |
| diRL-C10C10 | 81% by weight |
| diRL-C10C12 | 10% by weight |
| diRL-C10C12:1 | 8% by weight |
| monoRL-C10C10 | 1% by weight | resulting in a weight ratio of di-rhamnolipids to mono-rhamnolipids of 99:1.

Example 4

Testing the Skin Care Performance and Foam Properties by Means of a Hand Washing Test To assess the skin care performance and the foam properties of Product Examples 2 and 3 according to the invention in aqueous, surfactant compositions (surfactant formulations), sensory hand washing tests in comparison to known rhamnolipid compositions were performed.

A group of 10 trained testers washed their hands in a defined way during this hand washing test and assessed foam properties and hand feel by reference to a grading scale from 1 (poor) to 5 (very good). The products used were tested in each case in a standardized surfactant formulation (Table 1).

A surfactant formulation without the addition of a secondary surfactant was used as control formulation A. Surfactant formulations B and C are the comparison products not in accordance with the invention and surfactant formulations D and E are the compositions according to the invention (Table 1).

TABLE 1

Test formulations for hand washing test (data in % by weight).

| | Formulation examples | | | | |
|---|---|---|---|---|---|
| | A | B | C | D | E |
| Texapon ® NSO (BASF Cognis, INCI: Sodium Laureth Sulphate, 28% strength) | 32.1 | 32.1 | 32.1 | 32.1 | 32.1 |
| Example 1: pure diRL-C10C10 (not according to the invention) | | 3.0 | | | |
| Jeneil product (not according to the invention) | | | 3.0 | | |
| Example 2 (according to the invention) | | | | 3.0 | |
| Example 3 Fermentation product (according to the invention) | | | | | 3.0 |
| NaCl | 4.0 | 4.0 | 4.0 | 4.0 | 4.0 |
| Citric acid, 30% | | | ad pH 6.0 | | |
| Water, demineralized | | | ad 100% | | |

Table 2 shows the results of the hand washing test.

TABLE 2

Results of the hand washing test

| Test formulation | A | B | C | D | E |
|---|---|---|---|---|---|
| Foaming behavior | 2.7 | 3.2 | 2.6 | 3.4 | 3.5 |
| Foam volume | 2.6 | 2.7 | 2.3 | 2.7 | 2.7 |
| Foam creaminess | 2.1 | 2.7 | 2.4 | 2.9 | 3.0 |
| Skin feel during washing | 2.9 | 3.2 | 3.0 | 3.4 | 3.4 |
| Ease of wash-off | 3.8 | 3.5 | 3.1 | 3.4 | 3.4 |
| Skin feel directly after washing off | 2.4 | 2.0 | 2.2 | 2.3 | 2.3 |
| Skin smoothness after 3 min. | 2.8 | 3.3 | 3.1 | 3.5 | 3.7 |
| Skin softness after 3 min. | 2.9 | 3.4 | 3.1 | 3.5 | 3.7 |

It is evident from the measurement results in Table 2 that compositions D and E according to the invention using Product Examples 2 and 3 had a better skin feel during washing with the formulation and surprisingly also a better foaming behavior and increased foam creaminess compared to the control A and the comparison compositions B and C according to the prior art. Moreover, it was evident that compositions D and E according to the invention were assessed as being better than the comparison formulations for skin feel (skin smoothness and skin softness) after washing off and drying.

Contrary to expectations, a certain low fraction of monorhamnolipid in the biosurfactant exhibited a positive influence on the foam behavior and the skin feel in the present formulations.

Example 5

Testing the Foam Properties by Means of SITA Foam Tester

The ability of surfactant solutions to foam is an important parameter. Application properties can be inferred from this. A rapid foam formation and a large foam volume are expected in many applications from good surfactants. A method of evaluating this parameter is based on a SITA Foam Tester R-2000 from SITA Messtechnik GmbH. Here, air was introduced into a defined volume of a surfactant solution through a dispersing disc and the total volume of liquid and resulting foam was measured over the period by means of foam probes.

Three different rhamnolipid preparations were measured in such an instrument at pH=6 and a rhamnolipid total concentration of 0.5% by weight. The composition of the rhamnolipid fractions are listed in the table below.

| | E09-S6 | diRL-C10C10 | Jeneil |
|---|---|---|---|
| diRL-C8C10 | 21% by weight | 0% by weight | 2.1% by weight |
| monoRL-C8C10 | 0.9% by weight | 0% by weight | 1.9% by weight |
| diRL-C10C10 | 65% by weight | 100% by weight | 46.2% by weight |
| monoRL-C10C10 | 1.6% by weight | 0% by weight | 29.8% by weight |
| diRL-C10C12 | 6.0% by weight | 0% by weight | 7.8% by weight |
| monoRL-C10C12 | 0% by weight | 0% by weight | 5.6% by weight |
| diRL-C10C12:1 | 5.6% by weight | 0% by weight | 3.1% by weight |
| monoRL-C10C12:1 | 0% by weight | 0% by weight | 3.1% by weight |

A composition according to the invention E09-S6, which was obtained by fermentation, pure diRL-C10C10 and a commercially available product from Jeneil were investigated.

The measurements as regards foamability were carried out at a temperature of 30° C. with a liquid volume of 300 ml and a stirrer speed of 1500 rpm.

FIG. 1 shows that the foamability of E09 S6 was considerably better than that of the other samples, i.e., the maximum foam volume was achieved more quickly.

While the present invention has been particularly shown and described with respect to various embodiments thereof, it will be understood by those skilled in the art that the foregoing and other changes in forms and details may be made without departing from the spirit and scope of the present invention. It is therefore intended that the present invention not be limited to the exact forms and details described and illustrated, but fall within the scope of the appended claims.

What is claimed is:

1. A cosmetic composition comprising a mixture of rhamnolipids, wherein said mixture comprises
    51% by weight to 95% by weight of diRL-C10C10,
    0.5% by weight to 3% by weight of monoRL-C10C10,
    and 0.5 to 25% by weight of diRL-C10C12
    where the percentages by weight refer to the sum of all of the rhamnolipids present, and with the proviso that a weight ratio of said di-rhamnolipids to said monorhamnolipids is greater than 97:3, wherein said mixture comprises at tleast 60% by weight of rhamnolipids, and wherein the percentages by weight refer to the dry substance of the overall mixture.

2. The cosmetic composition according to claim 1, wherein said mixture further comprises
    0.1% by weight to 5% by weight of monoRL-C10C12,
    where the percentages by weight refer to the sum of all of the rhamnolipids present.

3. A cosmetic composition comprising a mixture of rhamnolipids, wherein said mixture comprises
0.5% by weight to 15% by weight of diRL-C10C12:1,
0.5 to 25% by weight of diRL-C10C12,
0.1% by weight to 5% by weight of monoRL-C10C12, and
0.1% by weight to 5% by weight of monoRL-C10C12:1,
where the percentages by weight refer to the sum of all of the rhamnolipids present.

4. The cosmetic composition according to claim 1, wherein said mixture further comprises
0% by weight to 5% by weight of diRLC10,
where the percentages by weight refer to the sum of all of the rhamnolipids present.

5. The cosmetic composition of claim 1, wherein said mixture further comprises
0.5% to 15% by weight of diRL-C10C12.1,
where the percentages by weight refer to the sum of all the rhamnolipids present.

6. A cosmetic composition comprising a mixture of mono-rhamnolipids and di-rhamnolipids, wherein a weight ratio of said di-rhamnolipids to said mono-rhamnolipids is greater than 97:3.

7. The cosmetic composition of any one of claims 1 and 6 further comprising at least one cosmetic active ingredient.

* * * * *